(12) United States Patent
Sakaguchi et al.

(10) Patent No.: US 6,635,787 B2
(45) Date of Patent: Oct. 21, 2003

(54) PRODUCTION METHOD OF A 2,6-DICHLOROPHENOL COMPOUND

(75) Inventors: Hiroshi Sakaguchi, Toyonaka (JP); Sanshiro Matsuo, Osaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/322,318

(22) Filed: Dec. 17, 2002

(65) Prior Publication Data

US 2003/0120119 A1 Jun. 26, 2003

(30) Foreign Application Priority Data

Dec. 20, 2001 (JP) ......................................... 2001-387259

(51) Int. Cl.$^7$ .............................................. C07C 41/22
(52) U.S. Cl. ........................................ 568/645; 568/649
(58) Field of Search .................................. 568/645, 649

(56) References Cited

U.S. PATENT DOCUMENTS

| 5,530,015 | A | * | 6/1996 | Sakamoto |
| 5,872,137 | A | | 2/1999 | Sakamoto et al. |
| 5,922,880 | A | | 7/1999 | Sakamoto et al. |
| 5,952,386 | A | * | 9/1999 | Matsuo |
| 6,140,274 | A | * | 10/2000 | Ikegami |
| 6,437,184 | B1 | * | 8/2002 | Ikegami |

FOREIGN PATENT DOCUMENTS

| JP | 52-027734 | 3/1977 |
| JP | 55-040613 | 3/1980 |
| JP | 06-025063 | 2/1994 |

OTHER PUBLICATIONS

J. Knuutinen et al., "Synthesis and Structure Verification of Chlorinated 4-Methoxyphenols, Models of Metabolites of Chlorophenolic Compounds", *Chemospere*, vol. 17, No. 9, pp 1821–1829 (1988).
T. Sohma and K. Konishi, "Studies on Organic Insecticides Part VIII. Synthesis of Alkoxyhalophenyl Benzenesulfonates", *Ann. Rept. Takeda Res. Lab.*, vol. 26, pp. 138–148 (1967) (No Translation).
Gnaim, J.M., et al., "Highly regioselective ortho–chlorination of phenol with sulfuryl chloride in the presence of amines," *Tetrahedron Letters*, vol. 36, No. 22, pp. 3893–3896 (1995).
*Chemical Abstracts*, "Synthesis of some ethers of halohydroquinones and halopyrocatechols," 45(22): 10213 (1951).
Brown, J.P., et al., "Some Chlorinated Hydroxyphenoxyacetic Acids," *Journal of the Chemical Society*, pp. 3681–3687 (1955).
Diana, Guy D., et al. "Antiviral Activity of Some β–Diketones. 2. Aryloxy Alkyl Diketones. In Vitro Activity against both RNA and DNA Viruses," *Journal of Medicinal Chemistry*, 20(6):757–761 (1977).

* cited by examiner

*Primary Examiner*—Michael L. Shippen
(74) *Attorney, Agent, or Firm*—Akin, Gump, Strauss, Hauer & Feld, L.L.P.

(57) ABSTRACT

A 2,6-dichlorophenol compound of formula (1):

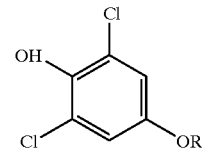

(1)

wherein R represents a 3,3-dihalo-2-propenyl group or a benzyl group optionally substituted by halogen atom(s), can be produced by making a phenol compound of formula (2):

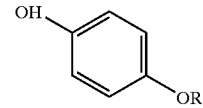

(2)

wherein R has the same meaning mentioned above, react with sulfuryl chloride in the presence of a secondary amine in high yield. The obtained 2,6-dichlorophenol compound of formula (1) is useful as intermediate for producing dihalopropene compounds having insecticidal/acaricidal activity.

10 Claims, No Drawings

PRODUCTION METHOD OF A 2,6-DICHLOROPHENOL COMPOUND

FIELD OF THE INVENTION

The present invention relates to production method of 2,6-dichlorophenol compounds.

BACKGROUND ARTS

It is described that a kind of 2,6-dichlorophenol compounds are useful for intermediates to prepare dihalopropene compounds having insecticidal/acaricidal activity in U.S. Pat. No. 5,872,137 and U.S. Pat. No. 5,922,880. According to the descriptions, said 2,6-dichlorophenol compounds can be given by making a phenol compound react with t-butyl hypochlorite. (cf. col.4, 80 and 126 in U.S. Pat. No. 5,872,137 and col. 83–84, 90 and 106 in U.S. Pat. No. 5,922,880).

However, this preparation method does not give high yield, and so it is not sufficient to prepare the objected 2,6-dichlorophenol compounds.

On the other hand, the 2,6-dichlorination of 4-alkylphenol with chlorine gas is described in JP-sho55-40613A and JP-sho52-27734A. Further, the chlorination of methoxyphenol is described in Chemosphere vol. 17,pp. 1821–1829 (1988) and Ann. Rept. Takeda Res. Lab. vol. 26,pp. 138–148 (1967).

The object of the present invention is to provide a production method of the 2,6-dichlorophenol compounds useful for intermediates to prepare the dihalopropene compounds having insecticidal/acaricidal activity.

SUMMARY OF THE INVENTION

The present invention provides a method for producing the 2,6-dichlorophenol compounds given by formula (1):

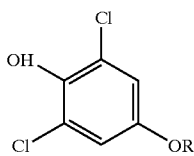

(1)

wherein R represents a 3,3-dihalo-2-propenyl group or a benzyl group optionally substituted by halogen atom(s), which comprises making a phenol compound given by formula (2):

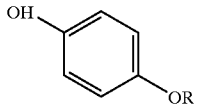

(2)

wherein R has the same meaning mentioned above, react with sulfuryl chloride in the presence of a secondary amine, and the method gives high yield of the product.

DETAILED DESCRIPTION OF THE INVENTION

In the present invention, the 3,3-dihalo-2-propenyl group for R is exemplified by 3,3-dichloro-2-propenyl group and 3,3-dibromo-2-propenyl group. Further, the benzyl group optionally substituted by halogen atom(s) is exemplified by a benzyl group whose hydrogen atom(s) on its benzene ring may be substituted by at least one halogen atom, and the typical examples are benzyl group and 4-chlorobenzyl group.

The present production method is characterized by the reaction of the phenol compound given by formula (2) with sulfuryl chloride in the presence of a secondary amine.

The reaction is usually carried out in a solvent. Examples of the solvent used for the reaction include aromatic hydrocarbons such as benzene, toluene, xylene, mesitylene, ethylbenzene and so on; aliphatic hydrocarbons such as hexane, heptane, octane and so on; halogenated aromatic hydrocarbons such as chlorobenzene, dichlorobenzene, benzotrifluoride and so on; and mixtures thereof.

Examples of the secondary amine used for the reaction include dialkylamine such as di(C2-C6)alkylamine; dialkenylamines such as di(C3-C6)alkenylamine; alkylalkenylamines such as (C2-C6)alkyl(C3-C6) alkenylamine; and dicycloalkylamines such as di(C3-C6)cycloalkylamine. Typical dialkylamines are diethylamine, dipropylamine, dibutylamine, dipentylamine, dihexylamine, diisopropylamine, di-sec-butylamine, ethylpropylamine and so on. Typical dialkenylamines are allylpropylamine, di(3-butenyl)amine and so on. Typical alkylalkenylamines are allylpropylamine and so on. Typical dicycloalkylamines are dicyclopropylamine, dicyclobutylamine, dicyclopentylamine, dicyclohexylalamine and so on The amount of the secondary amine used for the reaction is usually 0.001 to 1 mol based on 1 mol of the phenol compound given by formula (2), preferably 0.001 to 0.1 mol in the view of good operation for treatment after the reaction.

The amount of the sulfuryl chloride used for the reaction is usually 1.5 to 3.0 mols, preferably 2.0 to 2.5 mols based on 1 mol of the phenol compound given by formula (2) in the view of good yield.

The reaction temperature is usually in the range of 0 to 100° C., and the reaction period is usually in the range of 1 to 24 hours.

The reaction can be, for example, carried out by the followings.

1) A method of dissolving the phenol compound given by formula (2), the secondary amine and sulfuryl chloride in a solvent and stirring them.
2) A method of dissolving the phenol compound given by formula (2) and the secondary amine in a solvent and adding sulfuryl chloride dropwise to the solution under stirring.
3) A method of dissolving the secondary amine in a solvent, and adding the phenol compound given by formula (2) and sulfuryl chloride dropwise to the solution under stirring.

The status of the reaction can be confirmed by analyzing the reaction mixture by analyzing means such as high performance liquid chromatography, gas chromatography, thin layer chromatography and so on.

After the reaction, the work-up procedures, for example, mentioned below can make the 2,6-dichlorophenol compound given by formula (1) isolated.

1) Pouring the reaction mixture into acidic water (e.g. hydrochloric acid, aqueous sulfuric acid), separating the organic solvent from water and concentrating the obtained organic layer.
2) Pouring the reaction mixture into week basic water (e.g. aqueous sodium hydrogencarbonate), separating the organic solvent from water and concentrating the obtained organic layer.

3) Adding an aqueous solution of a reducing agent (e.g. sodium sulfite, sodium hydrogensulfite, sodium thiosulfate) to the reaction mixture, stirring for 0.1 to 24 hours at 0 to 100° C., separating the organic solvent from water and concentrating the obtained organic layer.

The isolated 2,6-dichlorophenol compound given by formula (1) can be further purified by column chromatography, recrystallization and so on.

EXAMPLES

The present invention is explained by examples below. The present invention is not restricted by these examples.

Example 1

5.05 g of 4-(3,3-dichloro-2-propenyloxy)phenol (purity: 99%) given by formula (3):

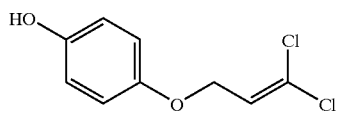

(3)

and 0.08 g of dicyclohexylamine were dissolved in 23.7 g of toluene, and 6.41 g of sulfuryl chloride was added dropwise at 65 to 70° C. under stirring over 5 hours. After the addition, the mixture was stirred at 65 to 70° C. for 3 hours. Then, 20 g of 10% aqueous sodium sulfite solution was added to the reaction mixture and further stirred at 65 to 70° C. for 1 hour. After allowing the reaction mixture to be cooled to room temperature, the organic layer was separated, washed with 5% hydrochloric acid, saturated brine and water subsequently, dried over anhydrous sodium sulfate and concentrated under reduced pressure to give 6.6 g of crude 2,6-dichloro-4-(3,3-dichloro-2-propenyloxy)phenol given by formula (4):

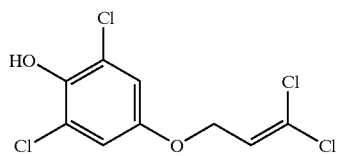

(4)

The crude product was analyzed with liquid chromatography to show 96% of the content (yield: 96%). 2,6-dichloro-4-(3,3-dichloro-2-propenyloxy)phenol $^1$H-NMR (CDCl$_3$/TMS) δ (ppm):4.57 (2H,d), 5.50 (1H, brs), 6.11 (1H,t), 6.85 (2H, s)

Example 2

4.38 g of 4-(3,3-dichloro-2-propenyloxy)phenol (purity: 100%) and 0.03 g of diethylamine were dissolved in 26.3 g of toluene, and 5.61 g of sulfuryl chloride was added dropwise thereto over 3 hours under stirring at 65 to 70° C. After the addition, the mixture was stirred for one hour at 65 to 70° C. After allowing the reaction mixture to be cooled to room temperature, 20g of aqueous saturated sodium hydrogencarbonate solution was added to the reaction mixture. The organic layer was separated, washed with 10 g of 5% hydrochloric acid and 10 g of water subsequently, and concentrated under reduced pressure to give 5.76 g of crude 2,6-dichloro-4-(3,3-dichloro-2-propenyloxy)phenol. The crude product was analyzed by liquid chromatography to show 95% of the content (yield: 95%).

Example 3

4.38g of 4-(3,3-dichloro-2-propenyloxy)phenol (purity: 100%) and 0.04 g of diislsopropylamine were dissolved in 26.3 g of toluene and 5.61 g of sulfuryl chloride was added thereto dropwise over 3 hours at 65 to 70° C. under stirring. After the addition, the mixture was stirred for one hour at 65 to 70° C. After allowing the reaction mixture to be cooled to room temperature, 20 g of aqueous saturated sodium hydrogencarbonate solution was added to the reaction mixture. The organic layer was separated, washed with 10 g of 5% hydrochloric acid and 10 g of water subsequently, and concentrated under reduced pressure to give 5.76 g of crude 2,6-dichloro-4-(3,3-dichloro-2-propenyloxy)phenol. The crude product was analyzed by liquid chromatography to show 96% of the content (yield: 96%).

Example 4

Ten grams (10.0 g) of 4-benzyloxyphenol (purity: 100%) and 0.18 g of dicyclohexylamine were dissolved in 43.25 g of toluene and 13.48 g of sulfuryl chloride was added dropwise thereto over 8 hours at 65 to 70° C. under stirring. After the addition, the mixture was stirred for one hour at 65 to 70° C. Then, 50 g of 10% aqueous sodium sulfite solution was added to the reaction mixture and further stirred at 65 to 70° C. for 1 hour. The organic layer was washed with 5% hydrochloric acid, saturated brine and water subsequently, dried over anhydrous sodium sulfate and concentrated under reduced pressure to give 13.1 g of crude 2,6-dichloro-4-benzyloxyphenol given by formula (5):

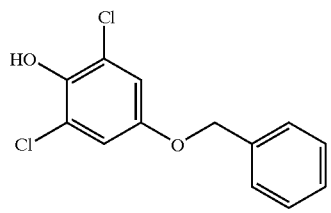

(5)

The crude product was analyzed by liquid chromatography to show 96% of the content (yield: 94%).

2,6-dichloro-4-benzyloxyphenol $^1$H-NMR (CDCl$_3$/TMS) δ (ppm):4.98(2H,s), 5.47(1H, s), 6.92(2H,s),7.39 (5H, s)

In the above examples, the content of the crude products was measured by the following analytical condition using diphenyl phthalate as an internal standard.

Device: Shimadzu GC-14A Gas Chromatography

Column: J & W Scientific DB-1 (0.53mmφx30m, membrane thickness: 1.5µ m)

Mobile phase: Helium 5ml/min.

Detector: FID

Injection Temperature: 300° C.

Detector Temperature: 300° C.

Column Temperature: 80° C. (5 min.)→10° C./min.→300° C. (20 min.)

According to the present production method, the 2,6-dichlorophenol compound given by formula (1), which is useful as intermediate for producing dihalopropene compounds having insecticidal/acaricidal activity, can be manufactured in high yield.

We claim:

1. A production method of a 2,6-dichlorophenol compound of formula (1):

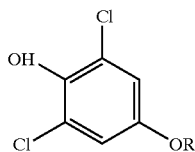
(1)

wherein R represents a 3,3-dihalo-2-propenyl group or a benzyl group optionally substituted by halogen atom(s), which comprises making a phenol compound of formula (2):

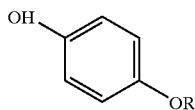
(2)

wherein R has the same meaning mentioned above, react with sulfuryl chloride in the presence of a secondary amine.

2. A production method according to claim 1, wherein R represents a 3,3-dihalo-2-propenyl group.

3. A production method according to claim 2, wherein R represents a 3,3-dichloro-2-propenyl group.

4. A production method according to claim 1, wherein R represents a benzyl group optionally substituted by at least one halogen atom.

5. A production method according to claim 4, wherein R represents a benzyl group or 4-chlorobenzyl group.

6. A production method according to claim 1, wherein the secondary amine is dialkylamine, dialkenylamine, alkylalkenylamine or dicycloalkylamine.

7. A production method according to claim 6, wherein the secondary amine is diethylamine, dipropylamine, dibutylamine, dipentylamine, dihexylamine, diisopropylamine, di-sec-butylamine, ethylpropylamine, diallylamine, di(3-butenyl)amine, allylpropylamine, dicyclopropylamine, dicyclobutylamine, dicyclopentylamine or dicyclohexylamine.

8. A production method according to claim 1, wherein the reaction temperature is in the range of 0 to 100° C.

9. A production method according to claim 1, wherein the molar ratio of the secondary amine to the phenol compound of formula (2) used for the reaction is 0.001:1 to 1:1.

10. A production method according to claim 1, wherein the molar ratio of the sulfuryl chloride to the phenol compound of formula (2) used for the reaction is 1.5:1 to 3.0:1.

* * * * *